(12) United States Patent
Rodgers et al.

(10) Patent No.: US 9,354,194 B2
(45) Date of Patent: May 31, 2016

(54) ORIENTATION INDEPENDENT METER

(71) Applicant: Cilag GmbH International, Zug (CH)

(72) Inventors: James Iain Rodgers, Inverness (GB);
Lawrence Ritchie, Inverness (GB);
Anna Zvikhachevskaya, Inverness
(GB); Jonathan Nelson, Inverness (GB);
Carlos Morales, West Chester, PA (US)

(73) Assignee: Cilag GmbH International, Zug (CH)

( * ) Notice: Subject to any disclaimer, the term of this patent is extended or adjusted under 35 U.S.C. 154(b) by 482 days.

(21) Appl. No.: 13/921,610

(22) Filed: Jun. 19, 2013

(65) Prior Publication Data

US 2014/0374278 A1     Dec. 25, 2014

(51) Int. Cl.
*G01N 27/327* (2006.01)

(52) U.S. Cl.
CPC ........ *G01N 27/3272* (2013.01); *G01N 27/3273* (2013.01)

(58) Field of Classification Search
CPC ..................... G01N 27/3272; G01N 27/3273
See application file for complete search history.

(56) References Cited

U.S. PATENT DOCUMENTS

| | | | |
|---|---|---|---|
| 4,714,874 A | 12/1987 | Morris et al. | |
| 5,264,103 A * | 11/1993 | Yoshioka | C12Q 1/004 204/403.1 |
| 5,526,120 A | 6/1996 | Jina et al. | |
| 6,235,241 B1 | 5/2001 | Catt et al. | |
| 6,335,203 B1 | 1/2002 | Patel et al. | |
| 6,349,230 B1 * | 2/2002 | Kawanaka | G01N 27/3272 204/403.14 |
| 6,458,596 B1 | 10/2002 | Poellmann | |
| 6,821,483 B2 | 11/2004 | Phillips et al. | |
| 6,964,871 B2 | 11/2005 | Bell et al. | |
| 7,327,451 B2 | 2/2008 | Markart | |
| 7,477,404 B2 | 1/2009 | Schulat et al. | |
| 7,527,716 B2 * | 5/2009 | Harding | C12Q 1/004 204/403.01 |
| 8,314,613 B2 | 11/2012 | Cui et al. | |
| 8,343,439 B2 | 1/2013 | Öhman et al. | |
| 8,409,424 B2 | 4/2013 | Chen et al. | |
| 8,465,635 B2 * | 6/2013 | Thurlemann | G01N 33/4905 204/403.01 |
| 2003/0169426 A1 | 9/2003 | Peterson et al. | |
| 2005/0247573 A1 * | 11/2005 | Nakamura | G01N 27/3272 205/777.5 |
| 2007/0040567 A1 | 2/2007 | Popovich et al. | |
| 2009/0084687 A1 | 4/2009 | Chatelier et al. | |
| 2009/0301899 A1 | 12/2009 | Hodges et al. | |

(Continued)

FOREIGN PATENT DOCUMENTS

| | | |
|---|---|---|
| EP | 0537761 A2 | 4/1993 |
| EP | 1065501 A1 | 1/2001 |

(Continued)

OTHER PUBLICATIONS

Lock, et al., 'Performance of a New Test Strip for FreeStyle Blood Glucose Monitoring Systems', *Diabetes Technology & Therapeutics*, vol. 13, No. 1, 10 pages, 2011.

(Continued)

*Primary Examiner* — Alexander Noguerola

(57) ABSTRACT

An analyte meter with a test strip port that detects an orientation of a test strip inserted therein. A control circuit of the test meter is configured to apply a first predetermined analyte measurement signal to a test strip electrode in response to detecting a first orientation of the test strip, and a second predetermined analyte measurement signal to the same, or a different, electrode in response to detecting a second orientation of the test strip.

2 Claims, 11 Drawing Sheets

(56) References Cited

U.S. PATENT DOCUMENTS

| | | |
|---|---|---|
| 2012/0048746 A1 | 3/2012 | Blythe et al. |
| 2012/0100601 A1 | 4/2012 | Simmons et al. |
| 2012/0267245 A1 | 10/2012 | Chambers et al. |

FOREIGN PATENT DOCUMENTS

| | | |
|---|---|---|
| EP | 1256798 A1 | 11/2002 |
| EP | 2153774 A | 2/2010 |
| WO | WO 2008134587 A1 | 11/2008 |
| WO | WO 2010063304 A1 | 6/2010 |
| WO | 2014037688 A1 | 3/2014 |

OTHER PUBLICATIONS

SureStep Technololgy 2011, *LifeScan Johnson& Johnson*. Available from: http://www.cliawaived.com/web/items/pdf/LifeScan_10797_Diabetes_Test~3038file1.pdf. [Sep. 28, 2011].

European Search Report issued in related European Patent Application No. 14173154.7, dated Oct. 31, 2014, 9 pages.

\* cited by examiner

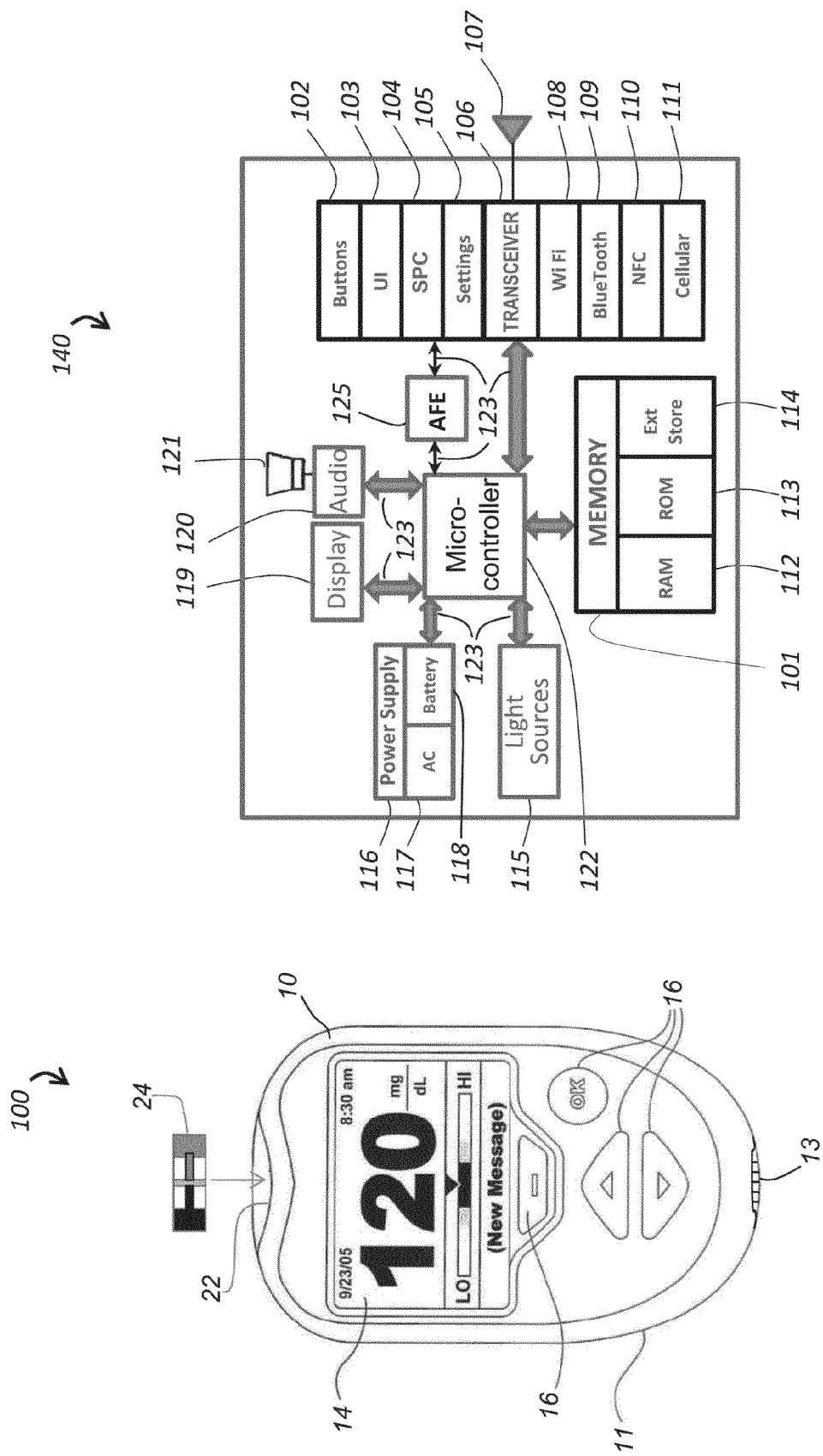

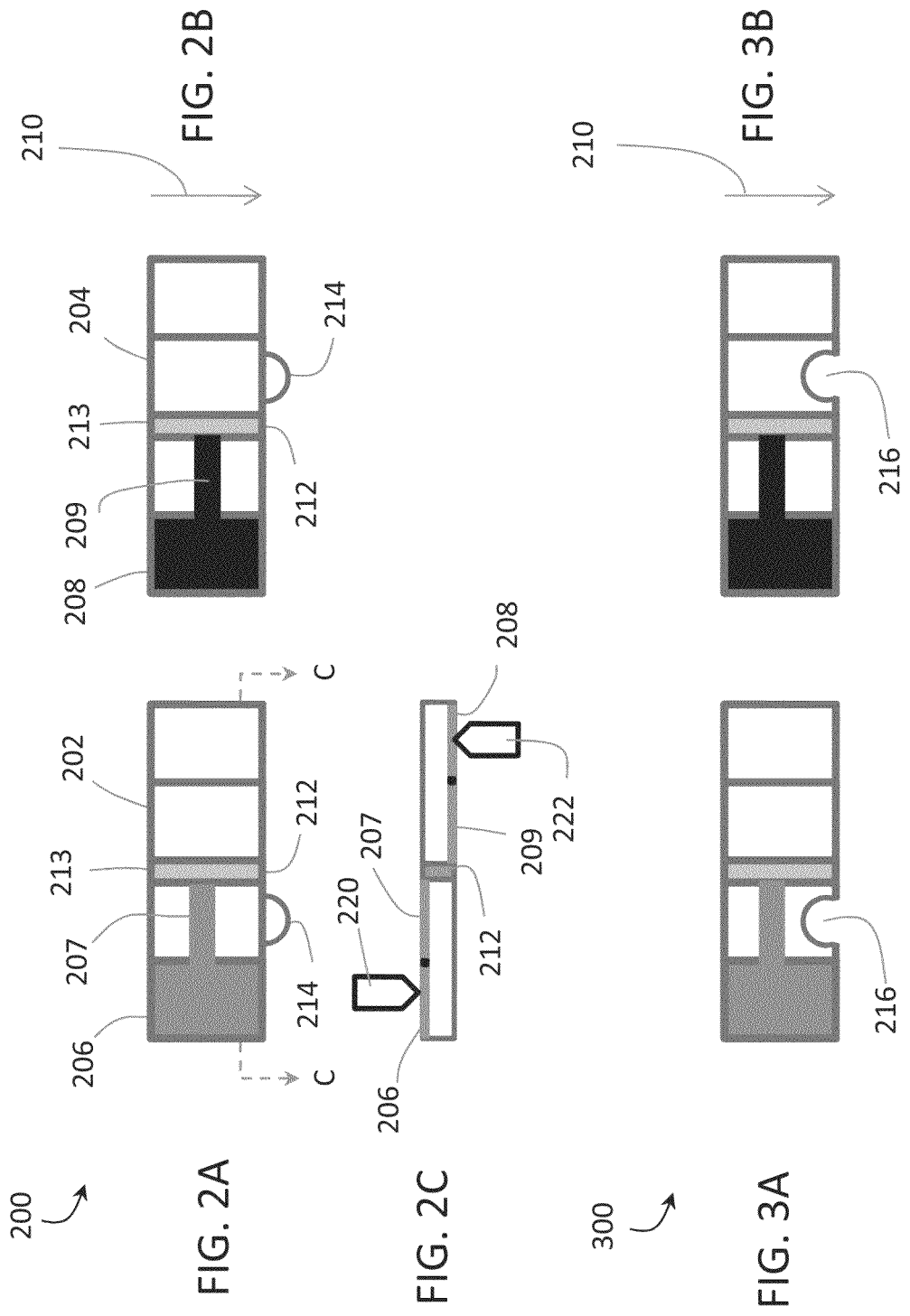

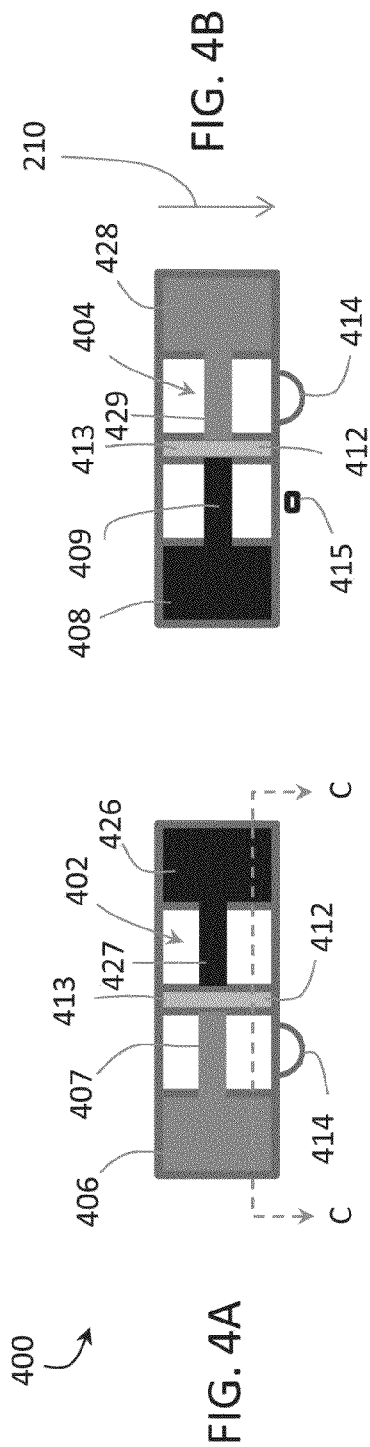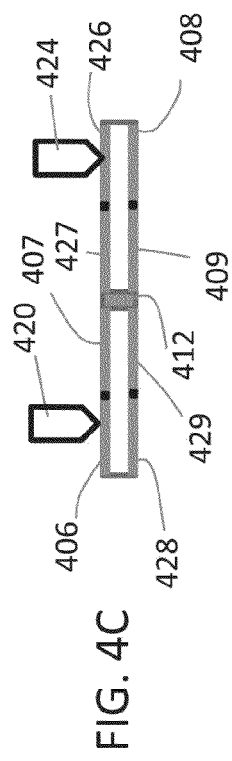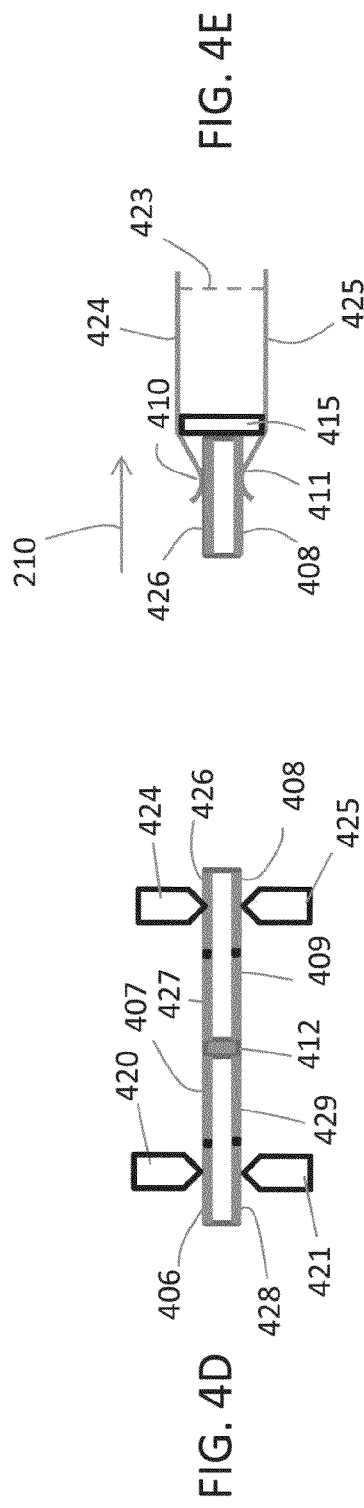

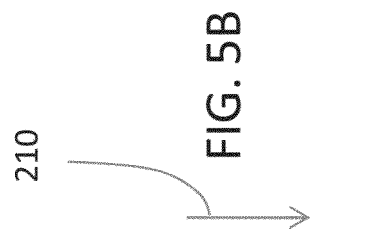
FIG. 5B
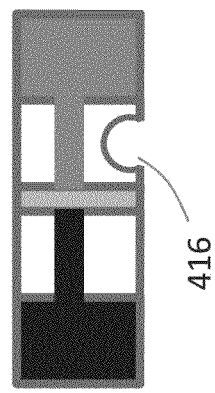
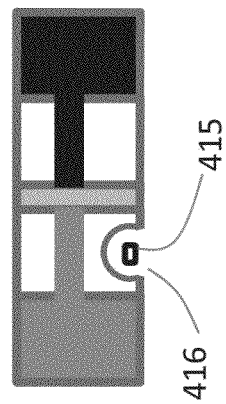
FIG. 5A

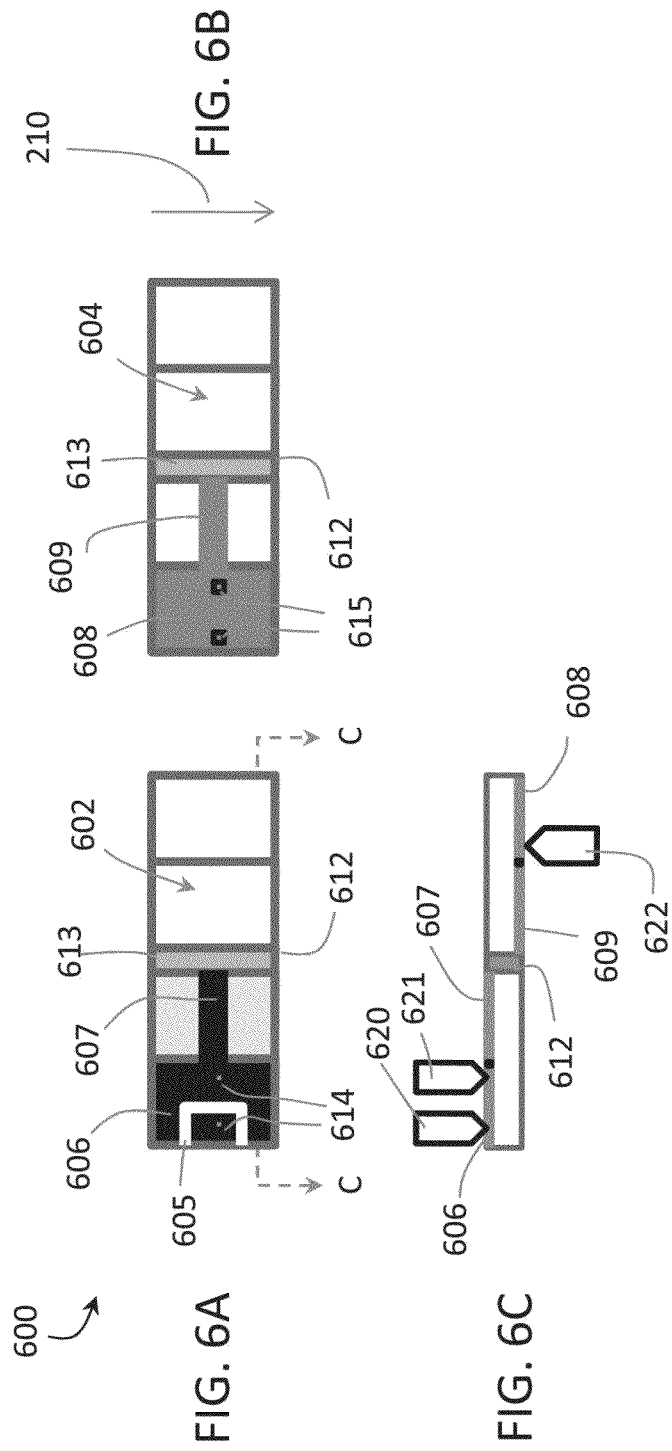

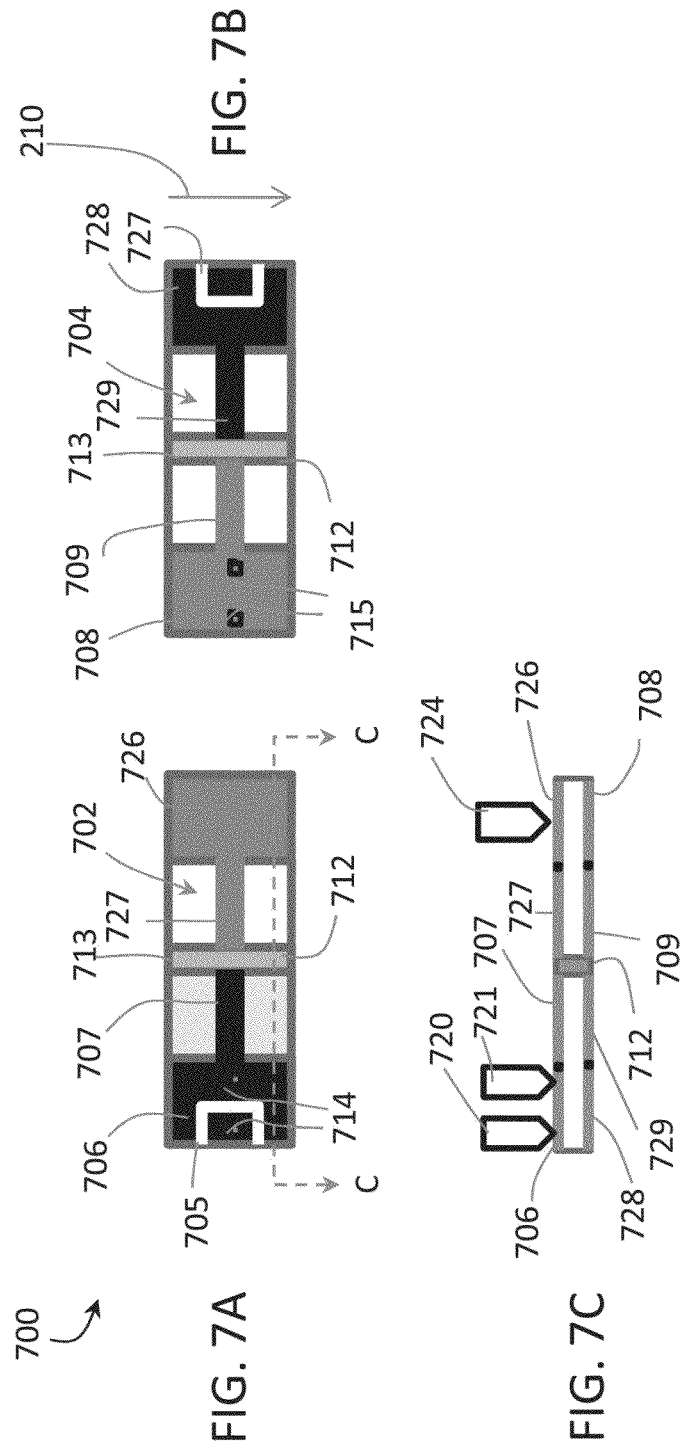

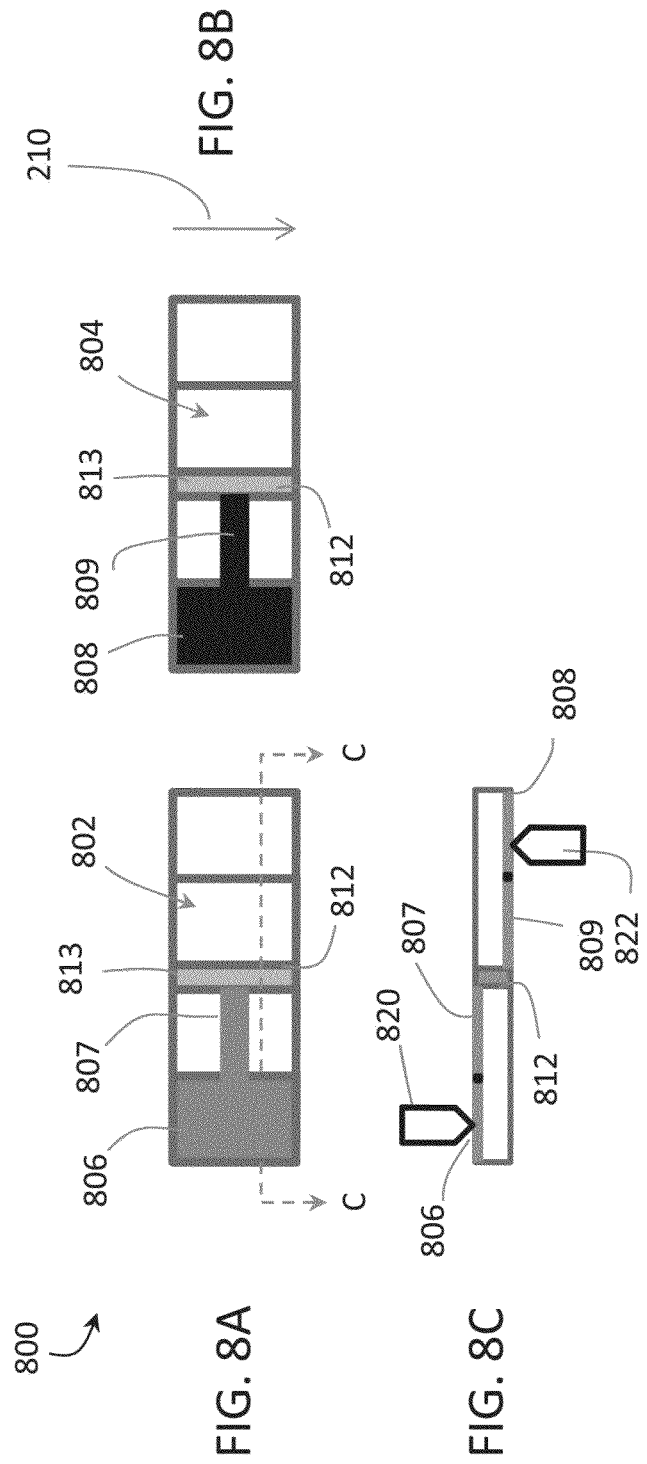

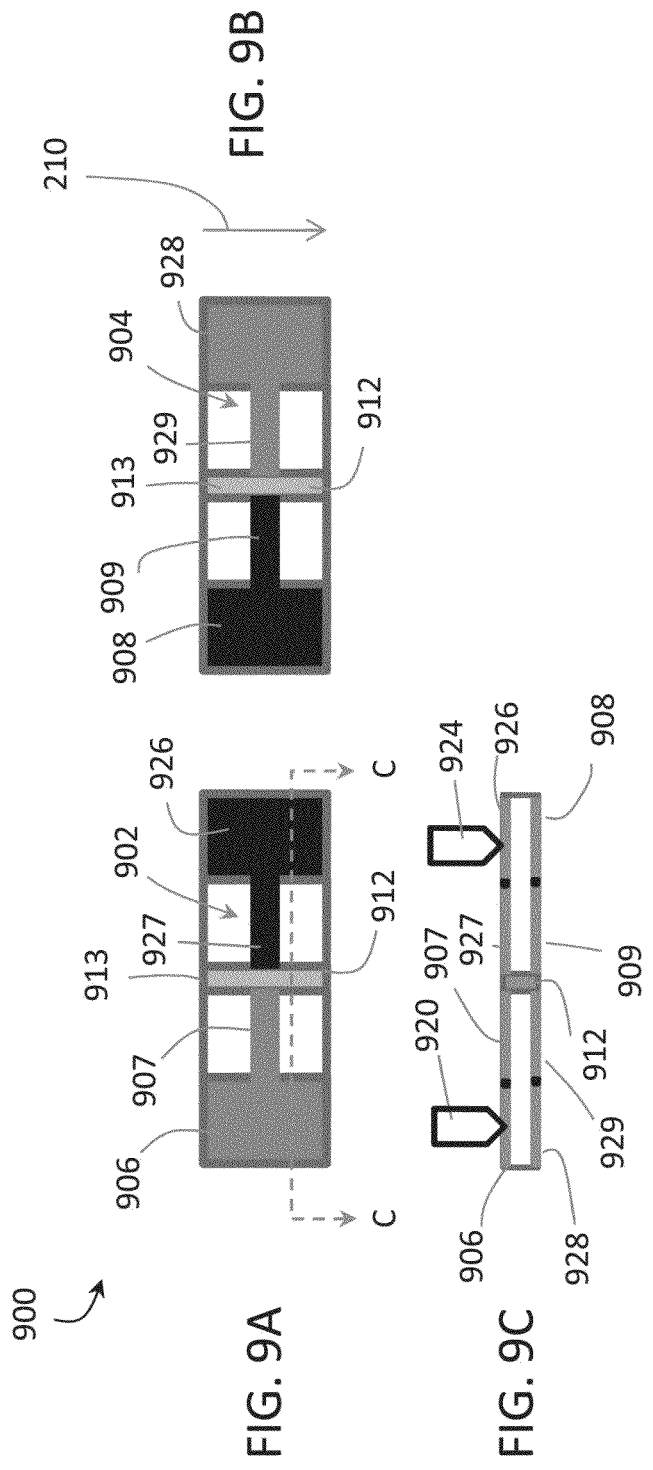

ORIENTATION INDEPENDENT METER

TECHNICAL FIELD

This application generally relates to the field of blood analyte measurement systems and more specifically to portable analyte meters that are configured to detect an orientation of a test strip inserted therein and to correctly adjust a test signal applied thereto in response to the detected orientation.

BACKGROUND

Blood glucose measurement systems typically comprise an analyte meter that is configured to receive a biosensor, usually in the form of a test strip. Because many of these systems are portable, and testing can be completed in a short amount of time, patients are able to use such devices in the normal course of their daily lives without significant interruption to their personal routines. A person with diabetes may measure their blood glucose levels several times a day as a part of a self management process to ensure glycemic control of their blood glucose within a target range. A failure to maintain target glycemic control can result in serious diabetes-related complications including cardiovascular disease, kidney disease, nerve damage and blindness.

There currently exist a number of available portable electronic analyte measurement devices that are designed to automatically activate upon insertion of a test strip. Electrical contacts, or prongs, in the meter establish connections with contact pads on the test strip while a microcontroller in the meter determines, based on electrical signals from the test strip, whether the test strip is properly inserted. Unless the test strip is properly inserted in a proper orientation, however, the device will not activate or, in addition, it may display an error message until the test strip is properly reinserted. This effort may present difficulty for some users who might struggle to correctly orient the test strip prior to insertion, particularly if the test strip is small.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1A illustrates a diagram of an exemplary test strip based analyte measurement system;

FIG. 1B illustrates a diagram of an exemplary processing system of the test strip based analyte measurement system of FIG. 1A;

FIGS. 2A-C illustrate various views of an exemplary test strip;

FIGS. 3A-B illustrate various views of another exemplary test strip;

FIGS. 4A-E illustrate various views of another exemplary test strip;

FIGS. 5A-B illustrate various views of another exemplary test strip;

FIGS. 6A-C illustrate various views of another exemplary test strip;

FIGS. 7A-C illustrate various views of another exemplary test strip;

FIGS. 8A-C illustrate various views of another exemplary test strip;

FIGS. 9A-C illustrate various views of another exemplary test strip;

MODES OF CARRYING OUT THE INVENTION

Figure 10:
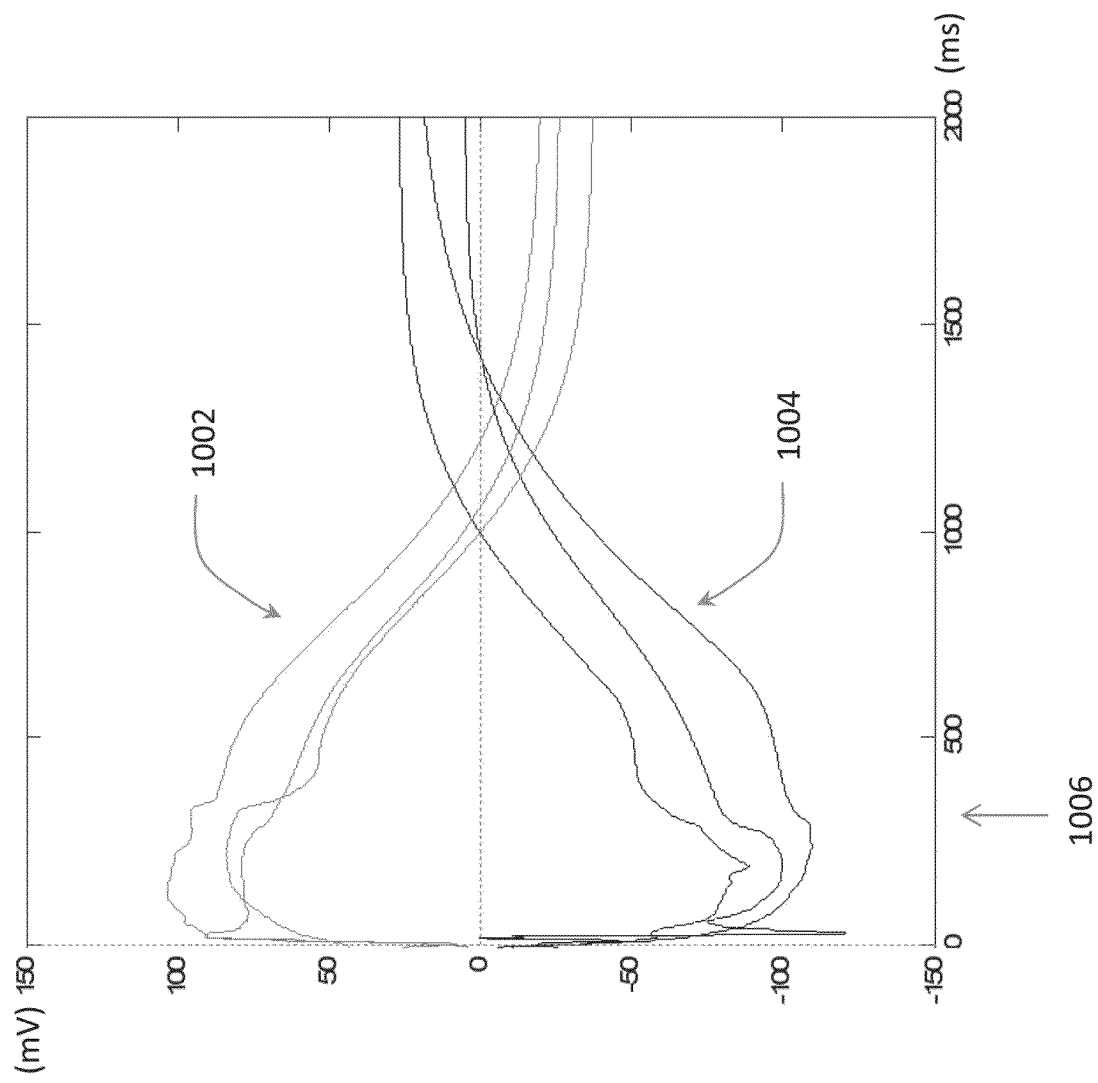
FIG. 10 illustrates exemplary voltage potential waveforms measured at the electrodes of the test strip depicted in FIGS. 8A-C and 9A-C.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component, the concentration of a component, e.g., an analyte, etc. The embodiments of the present invention are applicable to human and animal samples of whole blood. Typical samples in the context of the present invention as described herein include blood, plasma, red blood cells, serum and suspensions thereof.

The term "about" as used in connection with a numerical value throughout the description and claims denotes an interval of accuracy, familiar and acceptable to a person skilled in the art. The interval governing this term is preferably ±10%. Unless specified, the terms described above are not intended to narrow the scope of the invention as described herein and according to the claims.

FIG. 1A illustrates an analyte measurement system 100 that includes an analyte meter 10. The analyte meter 10 is defined by a housing 11 that retains a data management unit ("DMU") 140 and further includes a port 22 sized for receiving a biosensor. According to one embodiment, the analyte meter 10 may be a hand held blood glucose meter and the biosensor is provided in the form of a test strip 24 inserted into test strip port 22 for performing blood glucose measurements. The analyte meter 10 further includes a plurality of user interface buttons 16, and a display 14 as illustrated in FIG. 1A. A predetermined number of glucose test strips may be stored in the housing 11 and made accessible for use in blood glucose testing. The plurality of user interface buttons 16 are associated with the DMU 140 and can be configured to allow the entry of data, to prompt an output of data, to navigate menus presented on the display 14, and to execute commands. Output data can include values representative of analyte concentration presented on the display 14. Input information may include information related to the everyday lifestyle of an individual, such as food intake, medication use, occurrence of health check-ups, and general health condition and exercise levels of an individual. These inputs can be requested via prompts presented on the display 14 and can be stored in a memory module of the analyte meter 10. Specifically and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized.

The electronic components of the analyte measurement system 100 can be disposed on, for example, a printed circuit board situated within the housing 11 and forming the DMU 140 of the herein described system. FIG. 1B illustrates, in simplified schematic form, several of the electronic subsystems disposed within the housing 11 for purposes of this embodiment. The DMU 140 includes a processing unit 122 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below. The processing unit 122 is electrically connected to, for example, a test strip port connector 104 ("SPC") via an analog front end (AFE) subsystem 125. The AFE 125 is electrically connected to the strip port connector 104 during blood glucose testing. To measure a selected analyte concentration, the AFE 125 detects a resistance magnitude change across electrodes of analyte test strip 24 which indicates that a blood sample has been applied thereto, using a potentiostat. At a predetermined time after the blood sample has been applied to the test strip 24, a preset voltage waveform is applied across the sample via the electrodes which generates a an electric current therethrough. The AFE 125 converts the electric current measurement into digital form for presentation on the display 14. The processing unit 122 can be configured to receive input from the strip port connector 104, analog front end subsystem 125, and may also perform a portion of the potentiostat function and the current measurement function.

The analyte test strip 24 can be in the form of an electrochemical glucose test strip, of which various embodiments are described below. The test strip 24 is defined by a nonporous substrate that can include one or more working electrodes. Test strip 24 can also include a plurality of electrical contact pads, where each electrode can be in electrical communication with at least one electrical contact pad, as described below in relation to FIGS. 2A-9C. Strip port connector 104 can be configured to electrically interface to the electrical contact pads, using electrical contacts in the form of prongs, and form electrical communication with the electrodes. Test strip 24 can include a reagent layer that is disposed over one or more electrodes within the test strip 24, such as a working electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose in the applied sample into an enzymatic by-product and in the process generate an amount of reduced mediator (e.g., ferrocyanide) that is proportional to the glucose concentration of the sample. The working electrode can then be used to apply the preset voltage waveform to the sample and to measure a concentration of the reduced mediator in the form of an electric current. In turn, microcontroller 122 can convert the current magnitude into a glucose concentration for presentation on the display 14. An exemplary analyte meter performing such current measurements is described in U.S. Patent Application Publication No. US 2009/0301899 A1 entitled "System and Method for Measuring an Analyte in a Sample", which is incorporated by reference herein as if fully set forth in this application.

A display module 119, which may include a display processor and display buffer, is electrically connected to the processing unit 122 over the electrical interface 123 for receiving and displaying output data, and for displaying user interface input options under control of processing unit 122. The structure of the user interface, such as menu options, is stored in user interface module 103 and is accessible by processing unit 122 for presenting menu options to a user of the blood glucose measurement system 100. An audio module 120 includes a speaker 121 for outputting audio data received or stored by the DMU 140. Audio outputs can include, for example, notifications, reminders, and alarms, or may include audio data to be replayed in conjunction with display data presented on the display 14. Such stored audio data can be accessed by processing unit 122 and executed as playback data at appropriate times. A volume of the audio output is controlled by the processing unit 122, and the volume setting can be stored in settings module 105, as determined by the processor or as adjusted by the user. User input module 102 receives inputs via user interface buttons 16 which are processed and transmitted to the processing unit 122 over the electrical interface 123. The processing unit 122 may have electrical access to a digital time-of-day clock connected to the printed circuit board for recording dates and times of blood glucose measurements, which may then be accessed, uploaded, or displayed at a later time as necessary.

The display 14 can alternatively include a backlight whose brightness may be controlled by the processing unit 122 via a light source control module 115. Similarly, the user interface buttons 16 may also be illuminated using LED light sources electrically connected to processing unit 122 for controlling a light output of the buttons. The light source module 115 is electrically connected to the display backlight and processing unit 122. Default brightness settings of all light sources, as well as settings adjusted by the user, are stored in a settings module 105, which is accessible and adjustable by the processing unit 122.

A memory module 101, that includes but are not limited to volatile random access memory ("RAM") 112, a non-volatile memory 113, which may comprise read only memory ("ROM") or flash memory, and a circuit 114 for connecting to an external portable memory device, for example, via a USB data port, is electrically connected to the processing unit 122 over a electrical interface 123. External memory devices may include flash memory devices housed in thumb drives, portable hard disk drives, data cards, or any other form of electronic storage devices. The on-board memory can include various embedded applications and stored algorithms in the form of programs executed by the processing unit 122 for operation of the analyte meter 10, as will be explained below. On board memory can also be used to store a history of a user's blood glucose measurements including dates and times associated therewith. Using the wireless transmission capability of the analyte meter 10 or the data port 13, as described below, such measurement data can be transferred via wired or wireless transmission to connected computers or other processing devices.

A wireless module 106 may include transceiver circuits for wireless digital data transmission and reception via one or more internal digital antennas 107, and is electrically connected to the processing unit 122 over electrical interface 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 may be configured to detect a WiFi access point in proximity to the analyte meter 10 and to transmit and receive data from such a detected WiFi access point. A wireless transceiver circuit 109 may be compatible with the Bluetooth protocol and is configured to detect and process data transmitted from a Bluetooth beacon in proximity to the analyte meter 10. A wireless transceiver circuit 110 may be compatible with the near field communication ("NFC") standard and is configured to establish radio communication with, for example, another NFC compliant device in proximity to the analyte meter 10. A wireless transceiver circuit 111 may comprise a circuit for cellular communication with cellular networks and is configured to detect and link to available cellular communication towers.

A power supply module 116 is electrically connected to all modules in the housing 11 and to the processing unit 122 to supply electric power thereto. The power supply module 116 may comprise standard or rechargeable batteries 118 or an AC power supply 117 may be activated when the analyte meter 10 is connected to a source of AC power. The power supply module 116 is also electrically connected to processing unit 122 over the electrical interface 123 for supplying power thereto and so that processing unit 122 can monitor a power level remaining in a battery power mode of the power supply module 116.

FIGS. 2A-9C illustrate embodiments of a substantially flat (planar), elongated test strip 200 and strip port connector 104 that may be used for analyte measurement when the test strip 200 is inserted into a test strip port 22 of the analyte meter 100 in either of at least two orientations. With reference to FIGS. 2A-B, a test strip 200 is defined by opposing sides herein referred to as a top side 202 and a bottom side 204 of the test strip 200. Referring specifically to FIG. 2C, the test strip 200 having conductive contact pads 206, 208 disposed at opposite ends of the test strip 200, and in which contact pad 206 is provided on the top side 202 and contact pad 208 is provided on the bottom side 204 of the test strip 200. An arrow 210 indicates the direction of insertion of the test strip 200 into the test strip port 22, which may be inserted with either side 202, 204 of the test strip 200 facing upwardly. The test strip 200 includes a sample chamber 212 for receiving a sample therein provided by a user at one end 213 of the sample chamber 212. Electrodes 207, 209 extend from each contact pad 206, 208, respectively, to the sample chamber 212 wherein the sample provided therein makes physical contact with the electrodes 207, 209 and thereby establishes an electrical communication path between the contact pads 206, 208 on opposite ends and opposite sides 202, 204, of the test strip 200.

The analyte meter 100 that receives the test strip 200 in its test strip port 22 uses strip port connector 104 to make an electrical connection with the pair of the contact pads 206, 208 using contacts, such as prongs, 220, 222, respectively, that engage the contact pads 206, 208, of the test strip 200. One of the prongs 222 is disposed to contact the bottom side contact pad 208 while another prong 220 is configured to electrically connect with the top side contact pad 206 when the test strip 200 is inserted into the test strip port 22 in the first orientation. When the test strip 200 is inserted into the test strip port 22 in the second orientation, the prong 222 electrically connects with the top side contact pad 206 and the prong 220 electrically connects with the bottom side contact pad 208.

The illustrations of FIGS. 2A-C depict a test strip 200 whose orientation (i.e., first orientation or second orientation) is detected upon insertion into the test strip port 22 of the analyte meter 100. According to this embodiment, a projection, or lug, 214 disposed along a longitudinal edge of the test strip 200 may be sensed by the analyte meter 100 to determine the orientation of the test strip, for example, determining whether the top contact pad 206 faces upward or the bottom contact pad 208 faces upward, indicative of the first orientation and the second orientation, respectively. The first orientation, i.e., the top contact pad 206 facing upward, may be referred to herein as the default orientation. In one embodiment, the projection 214 may work in conjunction with a deflectable conductive element in the analyte meter, such as a conductive switch, that transmits a signal upon being deflected by the projection 214 when the test strip 200 is inserted in the test strip port 22 in one orientation, e.g., "top side up", and is not deflected if the test strip 200 is inserted into the test strip port 22 in a second orientation, e.g., "bottom side up". Alternatively, a sensing device, such as a mechanical microswitch, photodiode, capacitance sensor, or any other kind of detector may be used to detect the presence or absence of the projection 214. FIGS. 3A-B illustrate a test strip 300 that is similar in all respects to the test strip 200 just described with reference to FIGS. 2A-C, except that the projection 214 of the test strip 200 is replaced with an indentation 216 in the test strip 300. The indentation 216 may be used to detect an orientation of the test strip 300 at the time of its insertion into the analyte meter 100, in the direction indicated by arrow 210, such as by using any of the sensing devices identified above that detects the presence or absence of the indentation 216 of the test strip 300 at the time of insertion of the test strip 300 or, as described above with respect to the projection 214, a conductive deflectable element in the test strip port 22 of the analyte meter 100, such as a conductive switch, may be used to detect the indentation 216 wherein the indentation 216 positioned over the deflectable element fails to deflect it.

FIGS. 4A-E illustrate another embodiment of a substantially flat (planar), elongated test strip 400 and strip port connector 104 that may be used for analyte measurement when the test strip 400 is inserted into a test strip port 22 of the analyte meter 100 in either of at least two orientations. With reference to FIGS. 4A-B, a test strip 400 is defined by opposing sides herein referred to as a top side 402 and a bottom side 404 of the test strip 400. Referring specifically to FIG. 4C, the test strip 400 having conductive contact pads 406 and 428 at one end of the test strip 400, and contact pads 408 and 426 at an opposite end of the test strip 400, and in which contact pads 406 and 426 are provided on the top side 402, and contact pads 408 and 428 are provided on the bottom side 404 of the test strip 400. An arrow 210 indicates the direction of insertion of the test strip 400 into the test strip port 22, which may be inserted with either side 402, 404 of the test strip 400 facing upwardly. The test strip 400 includes a sample chamber 412 for receiving a sample therein provided by a user at one end 413 of the sample chamber 412. Electrodes 407, 427, 409, 429 extend from each contact pad 406, 426, 408, 428, respectively, to the sample chamber 412 wherein the sample provided therein makes physical contact with the electrodes 407, 427, 409, 429 and thereby establishes an electrical communication path between the contact pads 406, 408, 426, 428 on opposite ends and opposite sides 402, 404, of the test strip 400.

In one embodiment, illustrated in FIGS. 4A-C, the analyte meter 100 that receives the test strip 400 in its test strip port 22 may use strip port connector 104 to make an electrical connection with a pair of the contact pads, 406 and 426, or 408 and 428, using a strip port connector having at least one pair of electrical contacts, herein referred to as prongs, 420, 424 (FIG. 4C), that engage the corresponding pair of contact pads 406-426 or 408-428 on the same side 402, 404, respectively, of the test strip 400, depending on the orientation of the test strip 400 in the test strip port 22. The prongs 420, 424 are shown facing downward, but may also face upward to connect with the same pairs of contact pads 406-426 or 408-428 in the manner described herein.

In another embodiment, illustrated in FIGS. 4A-B and 4D-E, the analyte meter 100 that receives the test strip 400 in its test strip port 22 may use strip port connector 104 to make an electrical connection with the contact pads, 406, 426, 408, and 428, using a strip port connector having at least two sets of electrical contacts, herein referred to as prongs, 420, 424, and 421, 425, (FIG. 4D), that engage the corresponding pairs of contact pads 406-426 and 408-428 on the sides 402, 404, respectively, of the test strip 400, when the test strip 400 is inserted in a first (default) orientation in the test strip port 22. The test strip 400 may be inserted in a second orientation, in the manner described herein, wherein prongs, 420, 424, and 421, 425, engage the corresponding pairs of contact pads 408-428 and 426-406 on the sides 404, 402, respectively, of the test strip 400. FIG. 4E illustrates an end view of an embodiment of the two sets of prongs, 420, 424, and 421, 425, wherein upper prong 424 and lower prong 425 are visible in the perspective of FIG. 4E while upper prong 420 and lower prong 421 are similarly structured and positioned behind prongs 424, 425, respectively, in the view of FIG. 4E. The prongs, 420, 424, 421, and 425, comprise flexible spring arms, of which spring arms 410, 411 corresponding to prongs 424, 425, respectively, are visible in the perspective of FIG. 4. Such prongs may be fabricated from a conductive metallic material which flex in a direction away from the test strip 400 when the test strip is inserted therebetween by a user in the direction indicated by arrow 210. The prongs 424, 425 may be electrically shorted together by an optional electrical connector 423, as well as prongs 420, 421, by a corresponding electrical connector, thereby forming a single circuit node therewith of common voltage. The flexible spring arms 410, 411 provide enough compressive force to make electrical contact with contact pads 426, 408, respectively, (as well as spring arms corresponding to prongs 420, 421 making electrical contact with contact pads 406, 428, respectively) and to secure the test strip 400 therebetween when the test strip is inserted and when an analyte measurement process is undertaken by the meter 100, as described herein.

The illustrations of FIGS. 4A-E depict a system wherein an orientation of test strip 400 (i.e., first orientation or second orientation) is detected upon insertion into the test strip port 22 of the analyte meter 100. According to this embodiment, a projection, or lug, 414 disposed along a longitudinal edge of the test strip 400 may be sensed by the analyte meter 100 to determine the orientation of the test strip, for example, determining whether the top contact pads 406, 426 face upward or the bottom contact pads 408, 428 face upward, indicative of the first and second orientations, respectively. The first orientation, i.e., the top contact pads 406, 426 facing upward, may be referred to herein as the default orientation. In one embodiment, the projection 414 may work in conjunction with a sensing element 415 in the analyte meter, such as a conductive switch, that transmits a signal upon being deflected by the projection 414 when the test strip 400 is inserted in the test strip port 22 in one orientation, e.g., "top side up" and is not deflected if the test strip 400 is inserted into the test strip port 22 in a second orientation, e.g., "bottom side up". The sensing device 415 may be embodied as a mechanical microswitch, a deflectable conductive element, a photodiode, a capacitance sensor, or any other suitable detector to detect the presence or absence of the projection 414.

FIGS. 5A-B illustrate a test strip 500 that is similar in all respects to the test strip 400 just described with reference to FIGS. 4A-E, except that the projection 414 of the test strip 400 is replaced with an indentation 416 in the test strip 500. The indentation 416 may be used to detect an orientation of the test strip 500 at the time of its insertion into the analyte meter 100, in the direction indicated by arrow 210, for example, using a sensing device 415, such as a mechanical microswitch, photodiode, capacitance sensor, or any other kind of detector that senses the presence or absence of the indentation 416 of the test strip 500 or, as described above with respect to the projection 414, a deflectable element in the test strip port 22 of the analyte meter 100 may be used to detect the indentation 416 wherein the indentation 416 positioned over the deflectable element fails to deflect it. Although a projection 414 and an indentation 416 have been described as exemplary physical features that may be used to detect an orientation of a test strip 24, such examples should not be interpreted as limiting the embodiments described herein. Other detectable physical features may be formed or fabricated in the test strip 24 without departing from the spirit of the embodiments described herein. For example, a magnetic strip or indicator in the test strip 24 may be detected by a magnetic relay in the test strip port 22. Likewise, rotationally variant or invariant optical features may be printed or embedded in the test strip 24 which may be detected by optical readers, such as 1D or 2D barcode scanners, or an optical pattern matching system in the analyte meter 100, as a further example. In addition, the various mechanisms and methods described herein to determine test strip 24 orientation may be used in combination, which may serve as a verification of a determined test strip 24 orientation.

FIGS. 6A-C illustrate another embodiment of a substantially flat (planar), elongated test strip 600 and strip port connector 104 that may be used for analyte measurement when the test strip 600 is inserted into a test strip port 22 of the analyte meter 100 in either of at least two orientations. With reference to FIGS. 6A-B, the test strip 600 is defined by opposing sides herein referred to as a top side 602 and a bottom side 604 of the test strip 600. Referring specifically to FIG. 6C, the test strip 600 having conductive contact pads 606, 608 disposed at opposite ends of the test strip 600, and in which contact pad 606 is provided on the top side 602 and contact pad 208 is provided on the bottom side 604 of the test strip 600. An arrow 210 indicates the direction of insertion of the test strip 600 into the test strip port 22, which may be inserted with either side 602, 604 of the test strip 600 facing upwardly. The test strip 600 includes a sample chamber 612 for receiving a sample therein provided by a user at one end 613 of the sample chamber 612. Electrodes 607, 609 extend from each contact pad 606, 608, respectively, to the sample chamber 612 wherein the sample provided therein makes physical contact with the electrodes 607, 609 and thereby establishes an electrical communication path between the contact pads 606, 608 on opposite ends and opposite sides 602, 604, of the test strip 600.

One of the contact pads 606 comprises a border 605 that is non-conductive. This border 605 may be formed by ablation of the conductive material of the contact pad 606, such as using laser ablation, or, in another embodiment, the region surrounded by the non-conducive border 605 could be entirely formed as a non-conductive patch. The analyte meter 100 into which the test strip is inserted comprises two prongs 620, 621, proximate one end of the test strip 600, wherein one prong 620 is used for electrically contacting the region of the contact pad 606 within the border 605 and the other prong 621 for contacting the region of the contact pad 606 outside the border 605, when the top side 602 of the test strip is facing upward, as indicated by the contact points 614. A resistance between these two prongs 620, 621 of the analyte meter 100 can be measured while the prongs 620, 621 are physically simultaneously touching the region within the border 605 and the region outside the border 605 of contact pad 606, respectively. A high resistance will be measured because there is no conductive path between the prongs 620, 621 when they are touching contact points 614, thereby indicating the orientation of the test strip 600 as being "top side up". Thus, a first orientation of the test strip 600 may be determined based on the high resistance, and may be referred to herein as the default orientation.

The two prongs 620, 621, proximate one end of the test strip 600 may electrically connect to the contact pad 608 when the test strip 600 is inserted into the test strip port with the bottom side 604 facing upward (FIG. 6B) as indicated by the contact points 615. A resistance between the prongs 620, 621 of the analyte meter 100 can be measured while the prongs 620, 621 are physically simultaneously touching contact pad 608. A low resistance will be measured because contact pad 608 is entirely conductive, thereby indicating the orientation of the test strip 600 as being "bottom side up". Thus, a second orientation of the test strip 600 may be determined based on the low measured resistance. Based on these measured resistances using two prongs 620, 621 proximate one end of the test strip 600, analyte meter 100 may determine in which orientation the test strip 600 has been inserted.

The analyte meter 100 that receives the test strip 600 in its test strip port 22 uses strip port connector 104 to make an electrical connection with the contact pads 606, 608 using a strip port connector having at least one pair of electrical contacts, herein referred to as prongs, 621, 622, respectively, that engage the contact pads 606, 608, of the test strip 600. One of the prongs 622 is disposed to contact the bottom side contact pad 608 while another prong 621 is configured to electrically connect with the top side contact pad 606 when the test strip is inserted into the test strip port 22 in the first orientation. When the test strip 600 is inserted into the test strip port 22 in the second orientation, the prong 622 electrically connects with the top side contact pad 606 and the prong 621 electrically connects with the bottom side contact pad 608.

FIGS. 7A-C illustrate another embodiment of a substantially flat (planar), elongated test strip 700 and strip port connector 104 that may be used for analyte measurement when the test strip 700 is inserted into a test strip port 22 of the analyte meter 100 in either of at least two orientations. With reference to FIGS. 7A-B, a test strip 700 is defined by opposing sides herein referred to as a top side 702 and a bottom side 704 of the test strip 700. Referring specifically to FIG. 7C, the test strip 700 having conductive contact pads 706 and 728 at one end of the test strip 700, and contact pads 708 and 726 at an opposite end of the test strip 700, and in which contact pads 706 and 726 are provided on the top side 702, and contact pads 708 and 728 are provided on the bottom side 704 of the test strip 700. The arrow 210 indicates the direction of insertion of the test strip 700 into the test strip port 22, which may be inserted with either side 702, 704 of the test strip 700 facing upwardly. The test strip 700 includes a sample chamber 712 for receiving a sample therein provided by a user at one end 713 of the sample chamber 712. Electrodes 707, 709, 727, 729 extend from each contact pad 706, 708, 726, 728 respectively, to the sample chamber 712 wherein the sample provided therein makes physical contact with the electrodes 707, 727, 709, 729 and thereby establishes an electrical communication path between the contact pads 706, 708, 726, 728 on opposite ends and opposite sides 702, 704, of the test strip 700.

Two of the contact pads 706, 728 comprise a border 705, 727, respectively, that is non-conductive. These borders 705, 727, may be formed by ablation of the conductive material of the contact pads 706, 728, such as using laser ablation, or, in another embodiment, the region surrounded by the non-conducive borders 705, 727, could be entirely formed as a non-conductive patch. The analyte meter 100 into which the test strip 700 is inserted comprises two prongs 720, 721, proximate one end of the test strip 700. One of the prongs 720 is used for electrically contacting the region of the contact pad 706 within the border 705 and the other prong 721 for contacting the region of the contact pad 706 outside the border 705, when the top side 702 of the test strip is facing upward, as indicated by the contact points 714. A resistance between these two prongs 720, 721 of the analyte meter 100 can be measured while the prongs 720, 721 are physically simultaneously touching the region within the border 705 and the region outside the border 705 of contact pad 706, respectively. A high resistance will be measured because there is no conductive path between the prongs 720, 721 when they are touching contact points 714, thereby indicating the orientation of the test strip 700 as being "top side up". Thus, a first orientation of the test strip 700 may be determined based on the high resistance, and may be referred to herein as the default orientation.

The two prongs 720, 721, proximate one end of the test strip 700 may electrically connect to the contact pad 708 when the test strip 700 is inserted into the test strip port with the bottom side 704 facing upward (FIG. 7B) as indicated by the contact points 715. A resistance between the prongs 720, 721 of the analyte meter 100 can be measured while the prongs 720, 721 are physically simultaneously touching contact pad 708. A low resistance will be measured because contact pad 708 is entirely conductive, thereby indicating the orientation of the test strip 700 as being "bottom side up". Thus, a second orientation of the test strip 700 may be determined based on the low measured resistance. Based on these measured resistances using two prongs 720, 721 proximate one end of the test strip 700, analyte meter 100 may determine in which orientation the test strip 700 has been inserted.

The analyte meter 100 that receives the test strip 700 in its test strip port 22 uses strip port connector 104 to make an electrical connection with a pair of the contact pads, 706 and 726, or 708 and 728, using a strip port connector having at least one pair of electrical contacts, herein referred to as prongs, 721, 724, that engage the corresponding pair of the contact pads 706-726, or 708-728, on the same side 702, 704, respectively, of the test strip 700 depending on the orientation of the test strip 700 in the test strip port 22. The prongs 720, 721, 724 are shown facing downward, but may also face upward to electrically connect with the same pairs of contact pads 706-726, or 708-728 in the manner described herein.

FIGS. 8A-C illustrate embodiments of a substantially flat (planar), elongated test strip 800 and strip port connector 104 that may be used for analyte measurement when the test strip 800 is inserted into a test strip port 22 of the analyte meter 100 in either of at least two orientations. With reference to FIGS. 8A-B, a test strip 800 is defined by opposing sides herein referred to as a top side 802 and a bottom side 804 of the test strip 800. Referring specifically to FIG. 8C, the test strip 800 having conductive contact pads 806, 808 disposed at opposite ends of the test strip 800, and in which contact pad 806 is provided on the top side 802 and contact pad 808 is provided on the bottom side 804 of the test strip 800. An arrow 210 indicates the direction of insertion of the test strip 800 into the test strip port 22, which may be inserted with either side 802, 804 of the test strip 800 facing upwardly. The test strip 800 includes a sample chamber 812 for receiving a sample therein provided by a user at one end 813 of the sample chamber 812. Electrodes 807, 809 extend from each contact pad 806, 808, respectively, to the sample chamber 812 wherein the sample provided therein makes physical contact with the electrodes 807, 809 and thereby establishes an electrical communication path between the contact pads 806, 808 on opposite ends and opposite sides 802, 804, of the test strip 800.

The analyte meter 100 that receives the test strip 800 in its test strip port 22 uses strip port connector 104 to make an electrical connection with the pair of the contact pads 806, 808 using a strip port connector having at least one pair of electrical contacts, herein referred to as prongs, 820, 822, respectively, that engage the contact pads 806, 808, of the test strip 800. One of the prongs 822 is disposed to contact the bottom side contact pad 808 while another prong 820 is configured to connect with the top side contact pad 806 when the test strip 800 is inserted into the test strip port 22 in the first orientation, i.e., the "default" orientation. When the test strip 800 is inserted into the test strip port 22 in the second orientation, the prong 822 electrically connects with the top side contact pad 806 and the prong 820 electrically connects with the bottom side contact pad 808.

FIGS. 9A-C illustrate another embodiment of a substantially flat (planar), elongated test strip 900 and strip port connector 104 that may be used for analyte measurement when the test strip 900 is inserted into a test strip port 22 of the analyte meter 100 in either of at least two orientations. With reference to FIGS. 9A-B, a test strip 900 is defined by opposing sides herein referred to as a top side 902 and a bottom side 904 of the test strip 900. Referring specifically to FIG. 9C, the test strip 900 having conductive contact pads 906 and 928 at one end of the test strip 900, and contact pads 908 and 926 at an opposite end of the test strip 900, and in which contact pads 906 and 926 are provided on the top side 902, and contact pads 908 and 928 are provided on the bottom side 904 of the test strip 900. An arrow 210 indicates the direction of insertion of the test strip 900 into the test strip port 22, which may be inserted with either side 902, 904 of the test strip 900 facing upwardly. A default orientation of the test strip 900 may be referenced herein as the side 902 facing upwardly. The test strip 900 includes a sample chamber 912 for receiving a sample therein provided by a user at one end 913 of the sample chamber 912. Electrodes 907, 927, 909, 929 extend from each contact pad 906, 926, 908, 928, respectively, to the sample chamber 912 wherein the sample provided therein makes physical contact with the electrodes 907, 927, 909, 929 and thereby establishes an electrical communication path between the contact pads 906, 908, 926, 928 on opposite ends and opposite sides 902, 904, of the test strip 900.

The analyte meter 100 that receives the test strip 900 in its test strip port 22 uses strip port connector 104 to make an electrical connection with a pair of the contact pads 906 and 926, or 908 and 928, using a strip port connector having at least one pair of electrical contacts, herein referred to as prongs, 920, 924, that engage the corresponding pair of the contact pads 906-926, or 908-928, on the same side 902, 904, respectively, of the test strip 900 depending on the orientation of the test strip 900 in the test strip port 22. The prongs 920, 924 are shown facing downward, but may also face upward to connect with the same pairs of contact pads 906-926 or 908-928 in the manner described herein.

The illustrations in FIGS. 8A-C and 9A-C depict test strips 800, 900 whose orientation (i.e., first orientation or second orientation) is detected after insertion into the test strip port 22 of the analyte meter 100 and upon providing a sample in the sample chamber 812, 912. As described above, a mediator, that may include, for example, ferricyanide, is deposited on one of the electrodes in the test strip, namely, the working electrode, which will be designated as the electrodes 807 and 907, 909 in the exemplary test strips of FIGS. 8A, 9A, and 9B, respectively, although opposing electrodes corresponding to these may, instead, be designated as working electrodes. The mediator may comprise one or more components that mix with the sample upon application in the sample chamber 812, 912, and are used in the generation of a glucose measurement current therethrough using the electrodes 807, 809, and 907-927 or 909-929, via the analyte meter contacts 820, 822, and 920, 924, respectively, having been electrically connected to corresponding contact pads, as described herein. Such mixing of the mediator with the sample in the sample chamber takes a finite time until an equilibrated initial sample and mediator mixture is achieved in the sample chamber, during or after which time the glucose measurement input signal is applied to the mixture for the purpose of glucose testing. Immediately after the sample is applied to the sample chamber 812, 912 it establishes a physical connection with the corresponding electrodes, thereby electrochemically connecting the electrodes on opposite sides of the sample chamber 812, 912. The electrochemical characteristics as between the electrodes 807, 809, and 907-927 or 909-929, are asymmetric due to the mediator being present on only one of the electrodes, e.g. on electrode 807 of test strip 800 and on electrodes 907, 909 of test strip 900, for example. This results in a time duration during which the orientation of the test strip may be ascertained by detecting the asymmetric electrical or electrochemical property of these electrodes.

An example of the asymmetric electrical/electrochemical properties just described are illustrated in FIG. 10. In this example, time 0 on the horizontal axis, measured in milliseconds, indicates the time at which the sample is applied to the test strip 800, 900. Upon the provided sample making physical contact with electrodes 807, 809 of test strip 800 or electrodes 907, 927, and 909, 929 of test strip 900, for example, the voltage potential as measured between these electrodes is indicated by the voltage swings 1002, 1004 which occurs prior to the mediator mixing thoroughly with the provided sample. In this example embodiment, open circuit galvanostatic potentiometry is used to measure the voltage potential. The voltage swings 1002 and 1004 depicted in FIG. 10 illustrate six test cases, three in each of a positive and a negative going direction, that clearly demonstrate a detectable voltage potential generated by application of a sample in the test strip 800, 900. The voltage potential will swing toward the working electrode 807, or 907, 909, having the mediator deposited thereon. Thus, there exists a time duration of about two hundred (200) to three hundred (300) milliseconds 1006 after application of the sample to the test strip wherein the positive- or negative going voltage potential waveform reaches a positive or negative peak and may be easily and clearly detected by programmed operation of the microcontroller 122 to determine an orientation of the test strip 800, 900 in the test strip port 22 of the analyte meter 100. The positive or negative going voltage potential waveform may even be detected up to about 1000 milliseconds after application of the sample to the test strip. In the example graph illustrated in FIG. 10, the positive going voltage swings 1002 indicate a topside 802, 902 of a test strip 800, 900, respectively, facing downwardly. The negative going voltage swings 1004 indicate a topside 802, 902 of a test strip 800, 900, respectively, facing upwardly.

One advantage of using a short duration, e.g. less than 1 s duration or less than 300 ms, open circuit (0 amps) galvanostatic potentiometry is that it enables the potentiometric insertion orientation signal to be detected with minimal interference or impact upon the subsequent amperometric glucose measurement current because neither an external potential is applied nor current drawn from within the electrochemical cell over the duration of this orientation detection measurement phase.

In all of the above examples illustrated in FIGS. 2A-9C describing a determination of test strip 24 insertion orientation in the test strip port 22 of the analyte meter 100, after the orientation of the test strip is determined the glucose measurement current may be applied to the sample through the analyte meter 100 contact 220 in the example of FIG. 2C, the contact 420 in the example of FIG. 4C, the contact 621 in the example of FIG. 6C, the contact 721 in the example of FIG. 7C, the contact 820 n the example of FIG. 8C, and the contact 920 in the example of FIG. 9C. The glucose measurement current is applied in an appropriate polarity so that the blood glucose level may be measured correctly. The application of the correct polarity of a glucose measurement input signal includes the microcontroller 122 programmably controlling a circuit capable of inverting or not inverting the polarity the signal applied to the analyte meter 100 contact and thereby to a contact pad of the test strip 24 depending on the aforementioned determination of the orientation of the test strip 24.

Figures 11A, 11B:
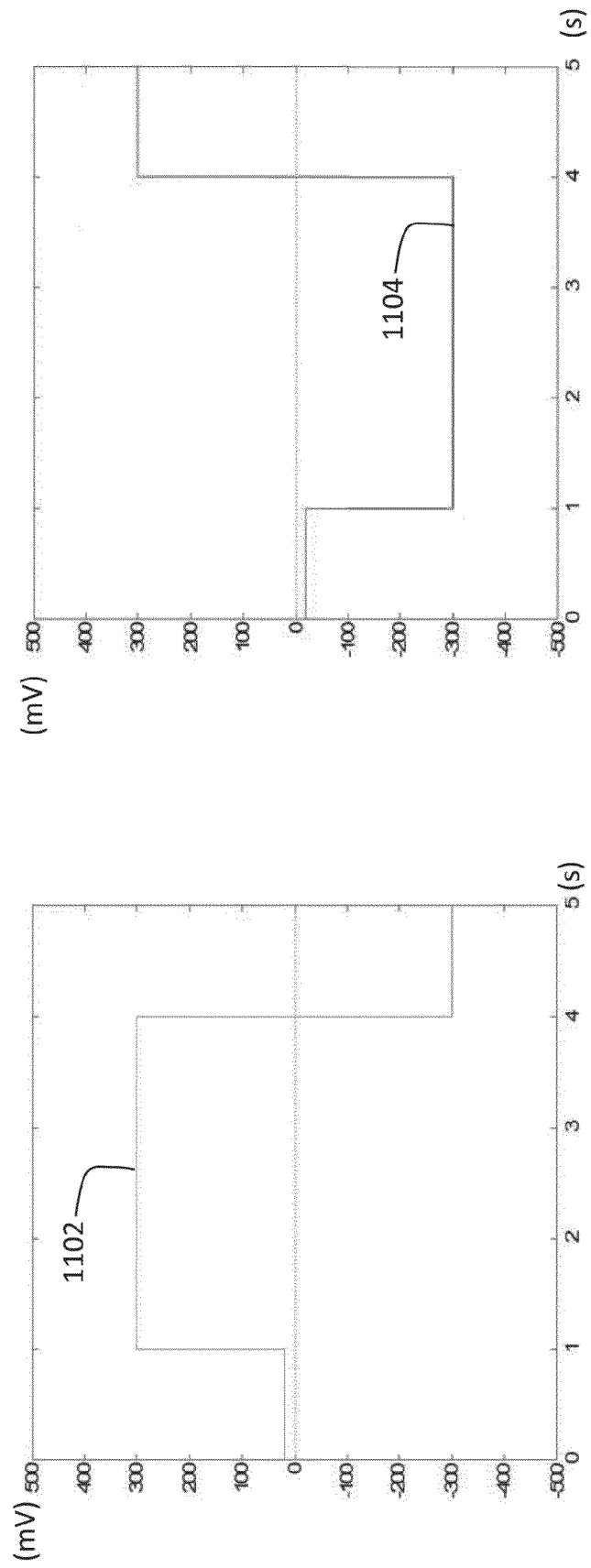
FIGS. 11A-B illustrate analyte current measurement voltages applied to the sample in a test strip depending on a determined orientation of the test strip.

FIG. 11A illustrates the input signal voltage 1102, i.e., the default analyte measurement input signal, controllably applied by the analyte meter 100 to the exemplary contacts identified above when the test strip 24 is inserted into the test strip port 22 top side up. FIG. 11B illustrates the analyte measurement input signal 1104 controllably applied by the analyte meter 100 to the exemplary contacts identified above when the test strip 24 is inserted into the test strip port 22 bottom side up. In one embodiment, the voltage applied to a top side up oriented test strip 24 includes a voltage of about +20 mV for about one second, followed by a voltage of about +300 mV for about three seconds, followed by a voltage level of about −300 mV for about one second. These applied voltages generate the glucose measurement current in the sample which is used to determine the glucose level of the sample, as described above. A test strip 24 determined to be oriented bottom side up in the analyte meter 100 would have the voltage waveform 1104 of FIG. 11B applied thereto, i.e., the inverse analyte measurement input signal, which is the inverse, or reverse polarity, of the default input signal waveform of FIG. 11A, through the analyte meter 100 contacts as identified above. An exemplary analyte meter applying such analyte measurement input signals for measuring glucose current is described in U.S. Patent Application Publication No. US 2009/0084687 A1 entitled "Systems and Methods of Discriminating Control Solution from a Physiological Sample", which is incorporated by reference herein as if fully set forth in this application.

Figure 12:
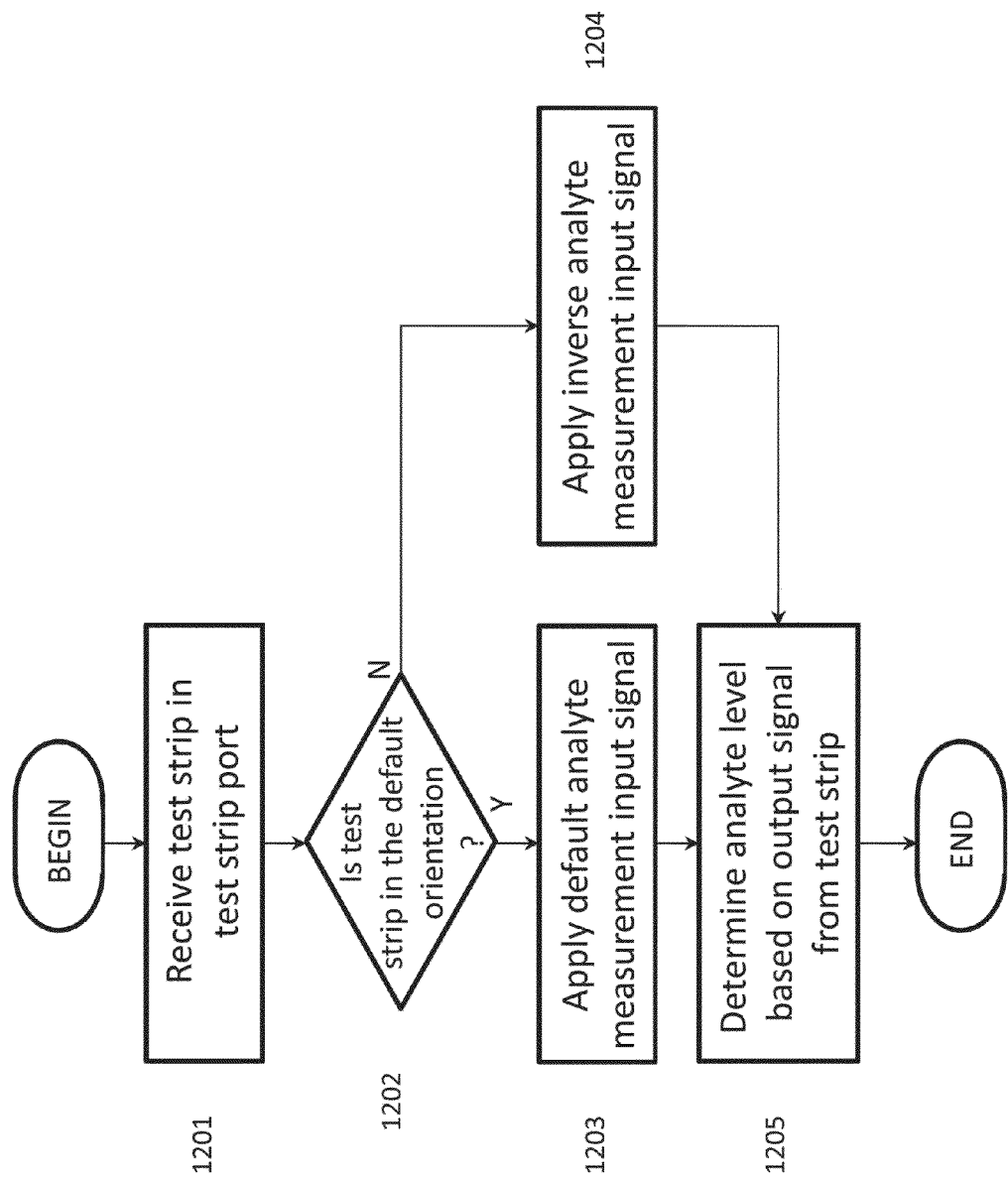
FIG. 12 illustrates a flow chart of a method of operating the analyte measurement system of FIGS. 1A-1B.

FIG. 12 illustrates an exemplary flow chart demonstrating a method of operating an analyte meter 100 as described herein. At step 1201 the analyte meter 100 receives a test strip 24 inserted into its test strip port 22. At step 1202 the analyte meter 100 determines the orientation of the test strip 24 as inserted using any of mechanical, optical, or electrical detection means as described herein, or a combination thereof. The determination step 1202 may be performed before or after a sample is applied to the test strip 24 depending upon whether the determination means requires the sample to be present so as to apply test signals thereto, as described above, or whether the test strip 24 includes physical features that are detected by the meter 100 upon insertion. If the test strip is determined to be in the default orientation at step 1202 then, upon receiving a sample in the sample chamber, the default analyte measurement input signal is applied to the sample at step 1203. If the test strip is determined not to be in the default orientation at step 1202 then, upon receiving a sample in the sample chamber, the inverse analyte measurement input signal (inverse of the default) is applied to the sample at step 1204. At step 1205 the analyte meter 100 receives an output signal from the test strip 24 corresponding to a current level flowing through the sample therein which is used by the analyte meter 100 to determine an analyte level of the sample.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," "subsystem" and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Furthermore, the various methods described herein can be used to generate software codes using off-the-shelf software development tools. The methods, however, may be transformed into other software languages depending on the requirements and the availability of new software languages for coding the methods.

PARTS LIST FOR FIGS. 1A-12

10 analyte meter
11 housing, meter
13 data port
14 display
16 user interface buttons
22 strip port connector
24 test strip
100 analyte measurement system
101 memory module
102 buttons module
103 user interface module
104 strip port connector
105 microcontroller settings module
106 transceiver module
107 antenna
108 WiFi module
109 Bluetooth module
110 NFC module
111 GSM module
112 RAM module
113 ROM module
114 external storage
115 light source module
116 power supply module
117 AC power supply
118 battery power supply
119 display module
120 audio module
121 speaker
122 microcontroller (processing unit)
123 communication interface
125 analog front end subsystem
140 data management unit
200 test strip
202 test strip top side
204 test strip bottom side
206 contact pad
207 electrode
208 contact pad
209 electrode
210 direction (arrow)
212 sample chamber
213 one end of sample chamber
214 projection (lug)
216 indentation
220 contact (prong)
222 contact (prong)
300 test strip
400 test strip
402 test strip top side
404 test strip bottom side
406 contact pad
407 electrode
408 contact pad
409 electrode
410 spring arm
411 spring arm
412 sample chamber
413 one end of sample chamber
414 projection (lug)
415 sensor for projection (lug) or indentation
416 indentation
420 contact (prong)
421 contact (prong)
423 electrical connector
424 contact (prong)
425 contact (prong)
426 contact pad
427 electrode
428 contact pad
429 electrode
500 test strip
600 test strip
602 test strip top side
604 test strip bottom side
605 non-conductive border
606 contact pad
607 electrode
608 contact pad
609 electrode
612 sample chamber
613 one end of sample chamber
614 contact points
615 contact points
620 contact (prong)
621 contact (prong)
622 contact (prong)
700 test strip
702 test strip top side
704 test strip bottom side
706 contact pad
707 electrode
708 contact pad
709 electrode
712 sample chamber
713 one end of sample chamber
714 contact points
715 contact points
720 contact (prong)
721 contact (prong)
724 contact (prong)
725 non-conductive border
726 contact pad
727 electrode
728 contact pad
729 electrode
800 test strip
802 test strip top side
804 test strip bottom side
806 contact pad
807 electrode
808 contact pad
809 electrode
812 sample chamber
813 one end of sample chamber
820 contact (prong)
822 contact (prong)
900 test strip
902 test strip top side
904 test strip bottom side
906 contact pad
907 electrode
908 contact pad 909 electrode
912 sample chamber
913 one end of sample chamber
920 contact (prong)
924 contact (prong)
926 contact pad
927 electrode
928 contact pad
929 electrode
1002 voltage swing (positive)
1004 voltage swing (negative)
1006 time point
1102 applied voltage waveform
1104 applied voltage waveform
1201 step—receive test strip in test strip port
1202 step—is test strip in default orientation
1203 step—apply default analyte measurement input signal
1204 step—apply inverse analyte measurement input signal
1205 step—determine analyte level based on signal received from test strip While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A test strip and strip port connector (SPC) system comprising:
    a test strip with a lug disposed on a longitudinal edge thereof; the test strip having electrical contact pads at least at one end of the test strip; and
    a strip port connector (SPC) including:
        a first set of electrical contacts configured to make operable contact with electrical contact pads of the test strip inserted into the SPC in a first orientation;
        a second set of electrical contacts configured to make operable contact with the electrical contact pads of the test strip inserted into the SPC in a second orientation; and
        a test strip orientation detection mechanism configured to distinguish the first and second orientations based on positioning of the lug in the SPC.

2. A method for employing a hand-held test meter with a test strip comprising:
    inserting the test strip into an strip port connector (SPC) of a hand-held meter, the test strip having a lug disposed on a longitudinal edge thereof and electrical contact pads at least at one end thereof;
    making electrical contact to electrical contact pads of the test strip using one of:
        a first set of electrical contacts configured to make operable contact with electrical contact pads of the test strip inserted into the SPC in a first orientation; and
        a second set of electrical contacts configured to make operable contact with the electrical contact pads of the test strip inserted into the SPC in a second orientation; and
    distinguishing the first and second orientations based on positioning of the lug in the SPC using a test strip orientation mechanism of the SPC.

* * * * *